(12) United States Patent
Guggenheim et al.

(10) Patent No.: US 11,220,480 B2
(45) Date of Patent: Jan. 11, 2022

(54) SYNTHESIS OF REACTIVE INTERMEDIATES FOR POLYETHERIMIDES, AND USES THEREOF

(71) Applicant: SHPP GLOBAL TECHNOLOGIES B.V., Bergen op Zoom (NL)

(72) Inventors: Thomas Link Guggenheim, Mt. Vernon, IN (US); Hendrich Chiong, Cincinnati, OH (US); Bernabe Quevedo Sanchez, Cartegena (ES); Carmen Rocio Misiego Arpa, Cartagena (ES); Juan Justino Rodriguez Ordonez, Cartagena (ES); Javier Nieves Remacha, Cartagena (ES)

(73) Assignee: SHPP GLOBAL TECHNOLOGIES B.V., Bergen op Zoom (NL)

( * ) Notice: Subject to any disclaimer, the term of this patent is extended or adjusted under 35 U.S.C. 154(b) by 255 days.

(21) Appl. No.: 16/474,256

(22) PCT Filed: Dec. 29, 2017

(86) PCT No.: PCT/US2017/068890
§ 371 (c)(1),
(2) Date: Jun. 27, 2019

(87) PCT Pub. No.: WO2018/126105
PCT Pub. Date: Jul. 5, 2018

(65) Prior Publication Data
US 2019/0315690 A1     Oct. 17, 2019

(30) Foreign Application Priority Data
Dec. 31, 2016    (EP) ..................................... 16382680

(51) Int. Cl.
C08G 73/10       (2006.01)
C07D 209/48     (2006.01)
C08G 79/08       (2006.01)

(52) U.S. Cl.
CPC ........... *C07D 209/48* (2013.01); *C08G 73/10* (2013.01); *C08G 73/1028* (2013.01); *C08G 73/1071* (2013.01); *C08G 79/08* (2013.01)

(58) Field of Classification Search
CPC ........ C08L 79/08; C08G 73/10; C07D 209/48
See application file for complete search history.

(56) References Cited

U.S. PATENT DOCUMENTS

| | | | |
|---|---|---|---|
| 4,167,506 A | 9/1979 | Shimada et al. | |
| 4,520,204 A | 5/1985 | Evans | |
| 4,581,396 A | 4/1986 | Sonnenberg | |
| 5,229,482 A | 7/1993 | Brunelle | |
| 5,264,520 A | 11/1993 | Mullins et al. | |
| 5,514,813 A | 5/1996 | Brunelle | |
| 5,663,275 A | 9/1997 | Schmidhauser | |
| 5,830,974 A | 11/1998 | Schmidhauser et al. | |
| 5,908,915 A | 6/1999 | Brunelle | |
| 5,917,005 A | 6/1999 | Brunelle et al. | |
| 6,028,159 A | 2/2000 | Suh et al. | |
| 6,031,061 A | 2/2000 | Suh et al. | |
| 6,066,743 A | 5/2000 | Nick et al. | |
| 6,235,866 B1 | 5/2001 | Khouri et al. | |
| 6,265,521 B1 | 7/2001 | Fyvie et al. | |
| 6,369,170 B1 | 4/2002 | Takekoshi | |
| 6,630,568 B1 | 10/2003 | Johnson et al. | |
| 6,790,934 B2 | 9/2004 | Johnson et al. | |
| 6,906,168 B2 | 6/2005 | Khouri et al. | |
| 6,919,418 B2 | 7/2005 | Khouri et al. | |
| 7,481,959 B2 | 1/2009 | Richards et al. | |
| 7,714,095 B2 | 5/2010 | Brunelle et al. | |
| 2003/0181756 A1 | 9/2003 | Colborn et al. | |
| 2004/0213980 A1 | 10/2004 | Babayan et al. | |
| 2005/0049384 A1 | 3/2005 | Khouri et al. | |

(Continued)

FOREIGN PATENT DOCUMENTS

| | | |
|---|---|---|
| CN | 1367192 A | 9/2002 |
| CN | 1396194 A | 2/2003 |

(Continued)

OTHER PUBLICATIONS

International Search Report; International Application No. PCT/US2017/068890; International Filing Date Dec. 29, 2017; dated Mar. 27, 2018, 5 pages.

(Continued)

*Primary Examiner* — Gregory Listvoyb
(74) *Attorney, Agent, or Firm* — Cantor Colburn LLP

(57) ABSTRACT

A method for producing a reactive intermediate composition, including: reacting a substituted phthalic anhydride of the formula (I) with a diamine of the formula $H_2N$—R—$NH_2$ in the presence of an aromatic dianhydride in an amount of 10 to 50 mole percent based on the total moles of anhydride functionality in the reaction; wherein the reacting is conducted in an aprotic solvent in a reactor, under conditions effective to produce the reactive intermediate composition; and wherein X comprises a halogen or a nitro group, and R comprises a $C_{6-36}$ aromatic hydrocarbon group or a halogenated derivative thereof, a straight or branched chain $C_{2-20}$ alkylene or a halogenated derivative thereof, or a $C_{3-8}$ cycloalkylene or a halogenated derivative thereof.

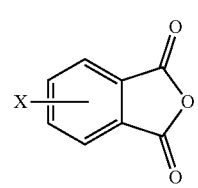

(I)

15 Claims, 1 Drawing Sheet

(56) References Cited

U.S. PATENT DOCUMENTS

| | | |
|---|---|---|
| 2005/0049390 A1 | 3/2005 | Brunelle et al. |
| 2006/0135731 A1 | 6/2006 | Silva et al. |
| 2006/0135741 A1 | 6/2006 | Gui et al. |
| 2008/0119660 A1 | 5/2008 | Khouri et al. |
| 2011/0263791 A1 | 10/2011 | Chiong et al. |
| 2011/0301320 A1 | 12/2011 | Hall |
| 2011/0303577 A1 | 12/2011 | Gallucci et al. |
| 2012/0127565 A1* | 5/2012 | Haralur ............... C08L 79/08 359/356 |
| 2013/0108852 A1 | 5/2013 | Kuhlman et al. |
| 2014/0094535 A1* | 4/2014 | Guggenheim .......... C08L 79/08 521/180 |
| 2014/0099510 A1 | 4/2014 | Chiong et al. |
| 2015/0079377 A1 | 3/2015 | Kuhlman |
| 2019/0031830 A1 | 1/2019 | Guggenheim et al. |

FOREIGN PATENT DOCUMENTS

| | | |
|---|---|---|
| CN | 1560113 A | 1/2005 |
| CN | 1803888 A | 7/2006 |
| CN | 101704950 A | 5/2010 |
| CN | 102030903 A | 4/2011 |
| EP | 0892003 A3 | 1/1999 |
| EP | 0866085 B1 | 6/2004 |
| JP | 5454140 S | 4/1979 |
| JP | 07216113 A | 8/1995 |
| WO | 0121685 A1 | 3/2001 |
| WO | 200121685 A1 | 3/2001 |
| WO | 0125196 A2 | 4/2001 |
| WO | 2009085824 A1 | 7/2009 |
| WO | 2013066757 A1 | 5/2013 |

OTHER PUBLICATIONS

Written Opinion of the Internation Searching Authority; International Application No. PCT/US2017/068890; International Filing Date Dec. 29, 2017; dated Mar. 27, 2018, 6 pages.

International Search Report for International Application No. PCT/US2017/015114, International Filing Date Jan. 26, 2017, dated May 11, 2017, 5 pages.

Non-Final Office Action for U.S. Appl. No. 16/073,505; Application Filing Date: Jul. 27, 2018; dated Apr. 7, 2020, 19 pages.

Written Opinion for International Application No. PCT/US2017/015114, International Filing Date Jan. 26, 2017, dated May 11, 2017, 8 pages.

\* cited by examiner

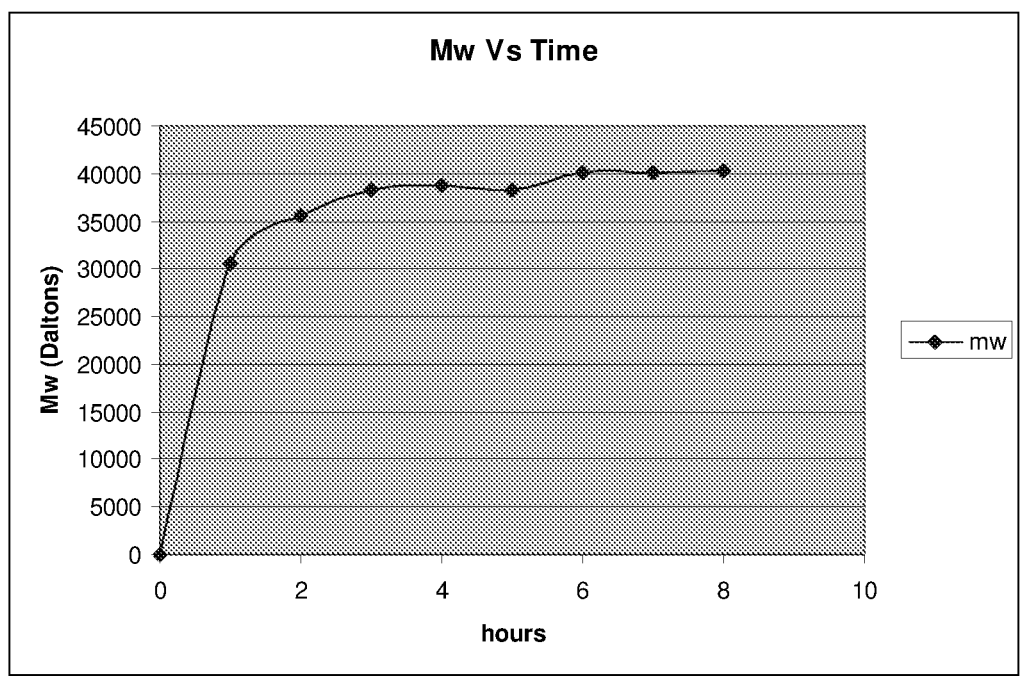

SYNTHESIS OF REACTIVE INTERMEDIATES FOR POLYETHERIMIDES, AND USES THEREOF

CROSS REFERENCE TO RELATED APPLICATIONS

This application is a National Stage application of PCT/US2017/068890, filed Dec. 29, 2017, which claims the benefit of European Application No. 16382680.3, filed Dec. 31, 2016, both of which are incorporated by reference in their entirety herein.

BACKGROUND

This disclosure relates to a method for the manufacture of reactive intermediates for the manufacture of polyetherimides.

One method for the manufacture of polyetherimides is known as the "displacement polymerization" process. Synthesis of polyetherimides via the displacement polymerization process includes imidization as described, for example, in U.S. Pat. No. 6,235,866, to produce a reactive bisphthalimide intermediate substituted with a leaving group; synthesis of a salt of a dihydroxy aromatic compound, as described, for example, in U.S. Pat. No. 4,520,204; and polymerization by reacting the substituted bisphthalimide and the salt, as described, for example, in U.S. Pat. No. 6,265,521.

In particular, imidization generally proceeds by reaction of 2 moles of a phthalic anhydride substituted with a leaving group with 1 mole of diamine in a reaction solvent, such as o-dichlorobenzene (oDCB). The reactive bisphthalimide intermediate is obtained as a slurry in the reaction solvent, which can be used directly in polymerization. The thixotropic nature of the bisphthalimide slurry causes adhesion to reactor walls and other internal equipment, such as stir shafts, stir blades, and baffles. This can lead to high levels of the reactive bisphthalimide intermediate contaminating the final polyetherimide product. It can further lead to other processing problems, such as difficulty in achieving thorough mixing and difficulty in sampling the reaction product. Further, the rate of polymerization is dependent on the dissolution rate of the bisphthalimide into the polymerization reaction mixture.

There accordingly remains a need in the art for improved imidization processes, in particular processes that would produce the bisphthalimide as a solution. It would be a further improvement if an intermediate composition was produced that does not adhere to the reaction vessel walls or internal equipment.

BRIEF DESCRIPTION

A method for producing a reactive intermediate composition, including: reacting a substituted phthalic anhydride of the formula

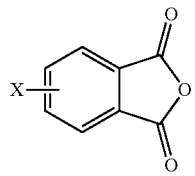

(1)

a diamine of the formula $$H_2N\text{—}R\text{—}NH_2 \quad (2)$$

in the presence of an aromatic dianhydride in an amount of 10 to 50 mole percent based on the total moles of anhydride functionality in the reaction; wherein the reacting is conducted in an aprotic solvent in a reactor, under conditions effective to produce the reactive intermediate composition; and wherein X comprises a halogen or a nitro group, and R comprises a $C_{6-20}$ aromatic hydrocarbon group or a halogenated derivative thereof, a straight or branched chain $C_{2-20}$ alkylene or a halogenated derivative thereof, or a $C_{3-8}$ cycloalkylene or a halogenated derivative thereof.

In another embodiment, a method of producing a polyetherimide comprises reacting the above-described reactive polyetherimide intermediate composition.

BRIEF DESCRIPTION OF THE DRAWINGS

The FIGURE is a graph of the molecular weight build in Example 1, as measured by gel permeation chromatography, versus time.

DETAILED DESCRIPTION

The inventors hereof have unexpectedly found that the presence of specific amounts of an aromatic dianhydride during imidization in the displacement polymerization process produces certain reactive polyetherimide intermediates that are more soluble in the reaction solvent. The components of the intermediate composition accordingly do not adhere to the reactor tank or its internal components, and are easier to mix and sample. In addition, the rate of subsequent polymerization is improved.

The amount of the aromatic dianhydride is from 10 to 50 mole percent (mol %), based on the total moles of anhydride functionality in the imidization reaction. In an especially advantageous feature, the aromatic anhydride can be selected to correspond to the structure of the salt of a dihydroxy aromatic compound incorporated into the polyetherimide product. The aromatic dianhydride is accordingly incorporated into the product polyetherimide, instead of requiring subsequent removal from the intermediate or polyetherimide compositions.

Accordingly, the imidization proceeds by reacting (condensing) a substituted phthalic anhydride and a diamine in an aprotic solvent, in the presence of an aromatic dianhydride. The substituted phthalic anhydride is of formula (1)

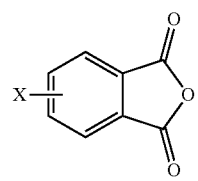

(1)

wherein X is a halogen, preferably bromine or chlorine, or a nitro group. In an embodiment, X is chlorine. In an embodiment, 4-chlorophthalic anhydride (4-ClPA) of formula (1a), 3-chlorophthalic anhydride (3-ClPA) of formula (1b) or a combination comprising at least one of the foregoing are used. In an embodiment, the substituted phthalic anhydride is a combination of 4-ClPA and 3-ClPA that includes 2 to 50%, preferably 10 to 50%, more preferably 25 to 50% of 3-ClPA.

(1a)
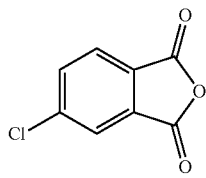

(1b)
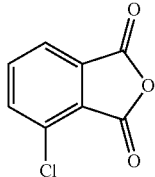

The diamine is of the formula (2)

$$H_2N-R-NH_2 \quad (2)$$

wherein R is substituted or unsubstituted divalent organic group, such as a $C_{6-20}$ aromatic hydrocarbon group or a halogenated derivative thereof, a straight or branched chain $C_{2-20}$ alkylene group or a halogenated derivative thereof, a $C_{3-8}$ cycloalkylene group or halogenated derivative thereof. In an embodiment, R is a divalent group of one or more of the following formulas (3)

(3)
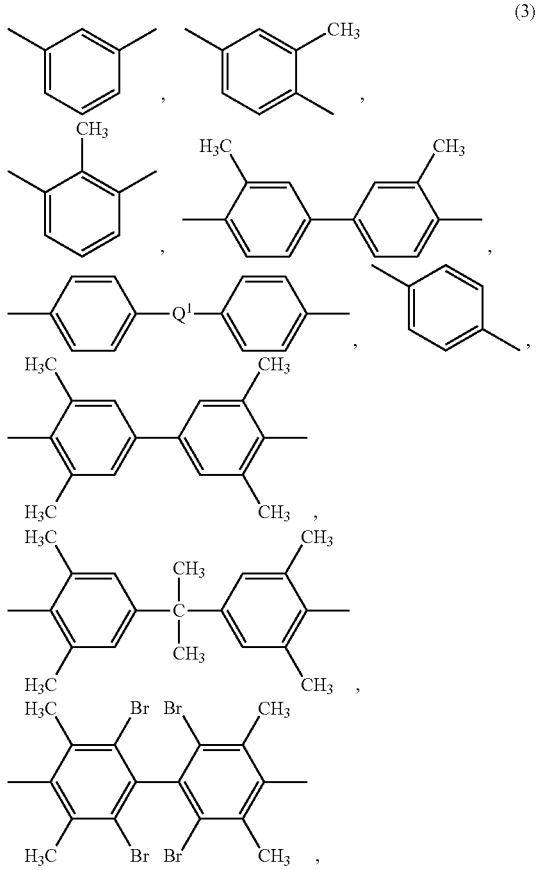

wherein $Q^1$ is —O—, —S—, —C(O)—, —SO$_2$—, —SO—, —P(R$^1$)(=O)— wherein R$^a$ is a $C_{1-8}$ alkyl or $C_{6-12}$ aryl, —C$_y$H$_{2y}$— wherein y is an integer from 1 to 5 or a halogenated derivative thereof, or —(C$_6$H$_{10}$)$_z$— wherein z is an integer from 1 to 4. In an embodiment R is m-phenylene, p-phenylene, or a diaryl sulfone, in particular bis(4,4'-phenylene)sulfone, bis(3,4'-phenylene)sulfone, bis(3,3'-phenylene)sulfone, or a combination comprising at least one of the foregoing. In an embodiment, at least 10 mole percent, or at least 50 mole percent of the R groups contain sulfone groups, and in other embodiments no R groups contain sulfone groups.

Examples of the diamines include 1,4-butane diamine, 1,5-pentanediamine, 1,6-hexanediamine, 1,7-heptanediamine, 1,8-octanediamine, 1,9-nonanediamine, 1,10-decanediamine, 1,12-dodecanediamine, 1,18-octadecanediamine, 3-methylheptamethylenediamine, 4,4-dimethylheptamethylenediamine, 4-methylnonamethylenediamine, 5-methylnonamethylenediamine, 2,5-dimethylhexamethylenediamine, 2,5-dimethylheptamethylenediamine, 2,2-dimethylpropylenediamine, N-methyl-bis (3-aminopropyl) amine, 3-methoxyhexamethylenediamine, 1,2-bis(3-aminopropoxy) ethane, bis(3-aminopropyl) sulfide, 1,4-cyclohexanediamine, bis-(4-aminocyclohexyl) methane, m-phenylenediamine, p-phenylenediamine, 2,4-diaminotoluene, 2,6-diaminotoluene, m-xylylenediamine, p-xylylenediamine, 2-methyl-4,6-diethyl-1,3-phenylene-diamine, 5-methyl-4,6-diethyl-1,3-phenylene-diamine, benzidine, 3,3'-dimethylbenzidine, 3,3'-dimethoxybenzidine, 1,5-diaminonaphthalene, bis(4-aminophenyl) methane, bis(2-chloro-4-amino-3,5-diethylphenyl) methane, bis(4-aminophenyl) propane, 2,4-bis(p-amino-t-butyl) toluene, bis(p-amino-t-butylphenyl) ether, bis(p-methyl-o-aminophenyl) benzene, bis(p-methyl-o-aminopentyl) benzene, 1,3-diamino-4-isopropylbenzene, bis(4-aminophenyl) sulfide, bis-(4-aminophenyl) sulfone (also known as 4,4'-diaminodiphenyl sulfone (DDS)), and bis(4-aminophenyl) ether. Any regioisomer of the foregoing compounds can be used. $C_{1-4}$ alkylated or poly($C_{1-4}$)alkylated derivatives of any of the foregoing can be used, for example a polymethylated 1,6-hexanediamine. Combinations of these compounds can also be used. In an embodiment the organic diamine is m-phenylenediamine, p-phenylenediamine, 4,4'-diaminodiphenyl sulfone, 3,4'-diaminodiphenyl sulfone, 3,3'-diaminodiphenyl sulfone, or a combination comprising at least one of the foregoing As stated above, the reaction proceeds in the presence of an aromatic dianhydride, for example an aromatic dianhydride of formula (4)

(4)
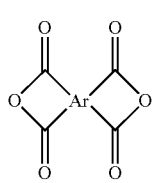

wherein Ar is a tetravalent $C_{6-36}$ hydrocarbon comprising at least one aromatic group, in particular a C6 aromatic group. Exemplary aromatic hydrocarbon groups include those of the formulas (5)

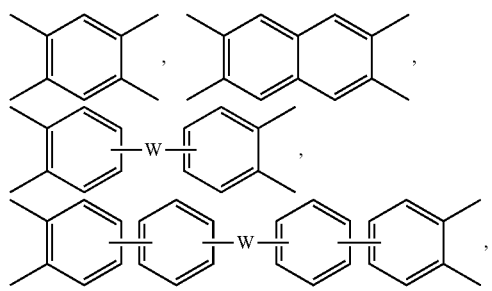
(5)

or a combination comprising at least one of the foregoing formulas, wherein W is a single bond, —O—, —S—, —C(O)—, —SO$_2$—, —SO—, a $C_{1-12}$ hydrocarbon moiety that can be cyclic, acyclic, aromatic, or non-aromatic, or —O—Z—O— wherein Z is a $C_{1-12}$ hydrocarbon moiety that can be cyclic, acyclic, aromatic, or non-aromatic. The $C_{1-12}$ hydrocarbon moiety can be disposed such that the $C_6$ arylene groups or oxygens connected thereto are each connected to a common alkylidene carbon or to different carbons of the $C_{1-18}$ hydrocarbon moiety. In an embodiment, Z is a $C_{1-8}$ aliphatic group or a $C_{6-12}$ aromatic group preferably a $C_{3-12}$ alkylidene or $C_{4-12}$ cycloalkylidene having a ring size of 4 to 6 carbon atoms. Any of the phenyl rings in the moieties of formulas (5) can be substituted with 0 to 4 halogen atoms or monovalent $C_{1-6}$ alkyl groups, for example methyl.

In an embodiment W is a single bond, —O—, —S(O)—, —S(O)$_2$—, —C(O)—, phenylene, or —O—Z$^1$—O— wherein $Z^1$ is a group of formula (6)

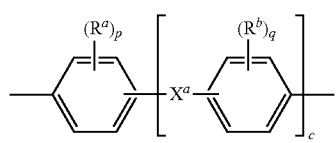
(6)

wherein $R^a$ and $R^b$ are each independently the same or different, and are a halogen atom or a monovalent $C_{1-6}$ alkyl group, for example; p and q are each independently integers of 0 to 4; c is 0 to 4; and $X^a$ is a bridging group connecting the hydroxy-substituted aromatic groups, where the bridging group and the hydroxy substituent of each $C_6$ arylene group are disposed ortho, meta, or para (o-, m-, or p-) to each other on the $C_6$ arylene group. In an embodiment, the bridging group and the hydroxyl substituent of each $C_6$ arylene group are disposed in a para configuration. The bridging group $X^a$ can be a single bond, —O—, —S—, —S(O)—, —S(O)$_2$—, —C(O)—, or a $C_{1-12}$ organic bridging group. The $C_{1-12}$ organic bridging group can be cyclic or acyclic, aromatic or non-aromatic, and can further comprise heteroatoms such as halogens, oxygen, nitrogen, sulfur, silicon, or phosphorous. The $C_{1-12}$ organic group can be disposed such that the $C_6$ arylene groups connected thereto are each connected to a common alkylidene carbon or to different carbons of the $C_{1-18}$ organic bridging group. A specific example of a group $Z^1$ is a divalent group of formula (6a)

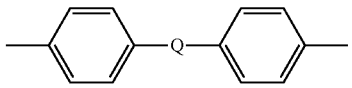
(6a)

wherein Q is —O—, —S—, —C(O)—, —SO$_2$—, —SO—, or —C$_y$H$_{2y}$— wherein y is an integer from 1 to 5 or a halogenated derivative thereof (including a perfluoroalkylene group). In a specific embodiment Q in formula (6) is 2,2-isopropylidene.

Examples of specific aromatic dianhydrides include 4,4'-bisphenol A dianhydride (also known as BPADA and 2,2-bis[4-(3,4-dicarboxyphenoxy)phenyl]propane dianhydride (CAS Registry No. 38103-06-9)); 3,4'-bisphenol A dianhydride (2,2-[4-(3-dicarboxyphenoxy)phenyl] 4-(4-dicarboxyphenoxy)phenyl]propane dianhydride); 3,3'-bisphenol A dianhydride (2,2-[3-(3,4-dicarboxyphenoxy)phenyl]propane dianhydride); 2,2-bis[4-(2,3-dicarboxyphenoxy)phenyl]propane dianhydride; 2,2-bis[4-(3,4-dicarboxyphenoxy)phenyl]butane dianhydride; 4,4'-oxydiphthalic anhydride (ODPA); 1,1,1,3,3,3-hexafluoro-2,2-bis[4-(3,4-dicarboxyphenoxy)phenyl]propane dianhydride (6FBPADA); 4,4'-(hexafluoroisopropylidene)diphthalic anhydride (6FDA); pyromellitic dianhydride (PMDA); hydroquinone diphthalic anhydride (HQDPA, 4,4'-(4,1-phenylenedioxy)bis[phthalic anhydride]); 3,3',4,4'-diphenyl sulfone tetracarboxylic dianhydride (DSDA); 3,3',4,4'-benzophenone tetracarboxylic dianhydride (BTDA); 3,3',4,4'-biphenyltetracarboxylic dianhydride (BPDA); 5,5'-[[1,1'-biphenyl]-4,4'-diylbis(oxy)]bis-1,3-isobenzofurandione (CAS Registry No. 26177-82-2)); 3,4,9,10-perylene-tetracarboxylic dianhydride, 1,4,5,8-naphthalenetetracarboxylic dianhydride, or a combination comprising at least one of the foregoing anhydrides.

Preferably the aromatic dianhydride is 4,4'-bisphenol A dianhydride, 4,4'-oxydiphthalic anhydride, pyromellitic dianhydride, hydroquinone diphthalic anhydride, 3,3',4,4'-diphenylsulfone tetracarboxylic dianhydride, diphenylsulfone tetracarboxylic dianhydride, benzophenonetetracarboxylic dianhydride, biphenyltetracarboxylic dianhydride, or a combination comprising at least one of the foregoing anhydrides. More preferably, the aromatic dianhydride is bisphenol A dianhydride, oxydiphthalic dianhydride, pyromelletic dianhydride, biphenyltetracarboxylic dianhydride, or a combination comprising at least one of the foregoing anhydrides.

The aromatic dianhydride is present in an amount of 10 to 50 mole percent, based on the total moles of anhydride functionality (i.e., the total moles of anhydride from the substituted phthalic anhydride and the aromatic dianhydride), 10 to 35 mole percent, based on the total moles of the anhydride functionality, 10 to 20 mole percent, based on the total moles of the anhydride functionality, or 20 to 30 mole percent, based on of the total moles of the anhydride functionality. When the aromatic dianhydride is present in lower amounts (e.g., less than 10 mole percent, based on the total moles of anhydride functionality), the bisphthalimide intermediates are not sufficiently soluble. Use of higher amounts of the aromatic dianhydride (e.g., greater than 50 mole percent, based on the total moles of anhydride functionality) is more costly, and decreases the rate of imidization.

The imidization can be conducted under conditions known to be effective to produce the bisphthalimide. Such conditions are described, for example, in U.S. Pat. Nos. 4,520,204; 5,229,482; 6,235,866 and U.S. Pat. No. 6,265,521.

A chain terminating agent can be present in the reaction mixture, in particular a monofunctional compound that can react with an amine or anhydride. Exemplary compounds that are amine-reactive include monofunctional aromatic anhydrides such as phthalic anhydride, an aliphatic monoanhydride such as maleic anhydride, or monofunctional aldehydes, ketones, esters, or isocyanates. A monofunctional bisphthalimide can also be added before or during imidization. The amount of monofunctional reactant that can be added depends on the desired amount of chain terminating agent. For example, the amount of monofunctional reactant present in the reaction can be more than 0 to 10 mole percent (mol %), or 0.1 to 10 mol %, or 0.1 to 6 mol %, based on the total moles of chain terminating agent and substituted phthalic anhydride.

The reaction is generally conducted in a relatively apolar, aprotic solvent, preferably with a boiling point above 100° C., specifically above 150° C., such as o-dichlorobenzene (oDCB), dichlorotoluene, 1,2,4-trichlorobenzene, diphenyl sulfone, sulfolane, or a monoalkoxybenzene such as anisole, veratrole, diphenylether, or phenetole. Preferably oDCB is used. In an embodiment, one or more of the other solvents can optionally be present with the oDCB, provided that the solvent(s) do not substantially adversely affect the desired solubilities and bisphthalimide intermediate yield.

Imidization can be conducted in the absence or in the presence of a phase transfer catalyst that is substantially stable under the reaction conditions used, in particular temperature. Exemplary phase transfer catalysts for polymerization include guanidinium salts such as hexa($C_{1-8}$alkyl)guanidinium and α,ω-bis(penta($C_{1-8}$alkyl)guanidinium)alkane salts. The counterion can be a halide, for example chloride.

Imidization is generally conducted at elevated temperature, for example at least 110° C., or 150° C. to 275° C., preferably 150° C. to 240° C., more preferably 175° C. to 225° C. At temperatures below 110° C., reaction rates may be too slow for economical operation. Atmospheric or super-atmospheric pressures can be used. For example, the reaction can be conducted at a pressure of up to 45 pounds per square inch (gauge)(psig) (up to 310.3 kilopascal (kPa)), or 1 to 30 psig (6.89 to 207 kPa), preferably 1 to 10 psig (6.89 to 68.9 kPa), more preferably 3 to 7 psig (20.7 to 48.3 kPa), to facilitate the use of high temperatures without causing solvent to be lost by evaporation.

Water removal from the system during imidization can be accomplished in batch, semi-continuous, or continuous processes using means known in the art such as a distillation column in conjunction with one or more reactors. In an embodiment, a mixture of water and non-polar solvent is distilled from a reactor and then is sent to a distillation column where water is taken off overhead and solvent is recycled back into the reactor at a rate to maintain or increase the desired solids concentration. Other methods for water removal include passing the condensed distillate through a drying bed for chemical or physical adsorption of water.

In general practice, a molar ratio of total anhydride groups (from both the substituted phthalic anhydride (1) and dianhydride (4)) to diamine (2) of 1.98:1 to 2.2:1, preferably 2.1:1 to 2:1, or 2:1. A slight excess of anhydride groups can be used to improve the color of the final product. A proper stoichiometric balance between the anhydride groups and diamine (8) is further maintained to prevent undesirable by-products that can limit the molecular weight of the polymer, and/or result in polymers with amine end groups. Accordingly, in an embodiment, imidization proceeds by adding diamine (2) to a combination of the substituted phthalic anhydride (1), the dianhydride (3), and solvent to form a reaction mixture having a targeted initial molar ratio of anhydride groups to diamine; heating the reaction mixture to a temperature of at least 100° C. (optionally in the presence of an imidization catalyst); analyzing the molar ratio of the heated reaction mixture to determine the actual initial molar ratio of anhydride groups to diamine; and, if necessary, adding substituted phthalic anhydride (1), dianhydride (4), or diamine (2) to the analyzed reaction mixture to adjust the molar ratio of anhydride groups to diamine to 1.98:1 to 2.2:1, preferably 2:1 to 2.1:1.

Imidization in the presence of the aromatic dianhydride results in a reactive intermediate composition that contains reactive intermediates that can be used in the manufacture of polyimides and polyetherimides. The reactive intermediates can include a bisphthalimide of formula (7)

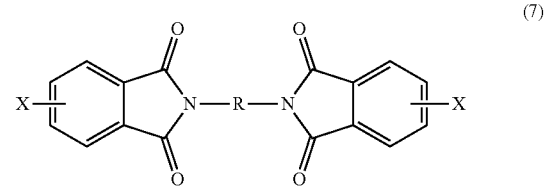

wherein X and R are as defined in formulas (1) and (2). The reactive intermediates can further include a polyphthalimide of formula (8)

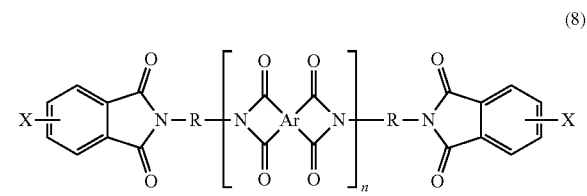

wherein R, Ar, and X are as defined in formulas (1), (2), and (4), and n is an integer greater than 1, for example 2 to 200, or 2 to 100, or 5 to 50. The value of n depends at least in part on reaction conditions and the amount of the aromatic dianhydride present during polymerization.

In an embodiment, the imidization produces 15 to 35 wt %, or 15 to 30 wt % total polyphthalimide, based on the total weight of the components (including solvent), also referred to herein as the reaction mass.

Surprisingly, the foregoing conditions can produce an end reactive intermediate composition wherein the reactive intermediates (7) and (8) are at least 80%, at least 90%, or at least 95% soluble on a weight basis in the reaction solvent at 180° C. at a range of 15 to 40 wt % solids, 20 to 40 wt % solids, 25 to 40 wt % solids, 30 to 40 wt % solids, or 25 to 35 wt % solids. The as-produced reactive intermediate composition is easy to stir, with no or substantially no sticking of material to the sides of the vessel or the stir shaft. The as-produced reactive intermediate composition can be allowed to cool to room temperature to provide a thicker slurry. Reheating the cooled reactive intermediate composition (e.g., to 180° C.) may not fully re-dissolve the reactive intermediates to the same extent as the as-produced composition. However, the slurry has a lower viscosity than a comparable reactive intermediate composition obtained by the same reaction conducted under the same conditions except in the absence the aromatic dianhydride (i.e., where the moles of anhydride groups supplied by the aromatic dianhydride have been replaced by equivalent moles of substituted phthalic anhydride (1)).

In a specific embodiment of the imidization, reaction of 4-ClPA (1a) with m-phenylene diamine, preferably in oDCB, in the presence of BPADA wherein BPADA provided 10 mol % of the anhydride groups, provides an on-stoichiometry reactive intermediate composition that includes a bischloro-terminated combination of reactive intermediates, in particular a combination comprising a bisphthalimide of formula (9) and a polyphthalimide of formula (10).

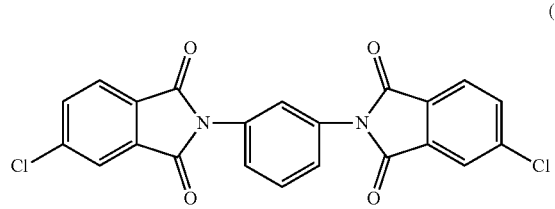

(9)

Other species can be present in the composition, including but not limited to residual substituted phthalic anhydride of formula (1) (e.g., 3-ClPA), residual chain terminating agent (e.g., phthalic anhydride, a monoamine, or phthalimide), or monoamines resulting from the incomplete reaction of mPD with a substituted phthalic anhydride of formula (1) (o e.g., phthalimide), or with one molecule of 3- or 4-ClPA). Surprisingly, the combination of bisphthalimide intermediates was nearly soluble in oDCB at 180° C. at 17 wt % solids. The mixture remained nearly completely soluble while maintained at 180° C. at 17 wt % solids with stirring. The initial solution was easy to stir and there was no sticking of material to the sides of the vessel or the stir shaft. The reaction mixture was allowed to cool to room temperature, where upon the reaction mixture became a thick slurry. The mixture was reheated to 180° C. and the reactive intermediates did not re-dissolve to the original extent observed when the mixture was initially synthesized, but the slurry was less thick than a comparable reaction product slurry made under the same conditions, using ClPA in oDCB, in the absence of an aromatic dianhydride, where the moles of anhydride groups supplied by the BPADA were replaced by equivalent moles of 4-ClPA.

The reactive intermediate composition can be used in the manufacture of polyetherimides by reaction with an alkali metal salt of a dihydroxy aromatic compound. In particular, the group X of the reactive intermediates is displaced by reaction with an alkali metal salt is of formula (11)

$$M^1O-Z^1-OM^1 \tag{11}$$

wherein each $M^1$ is independently an alkali metal, for example lithium, sodium, potassium, or cesium. In an embodiment, each $M^1$ is potassium or sodium, preferably sodium, and $Z^1$ is as defined in formula (6). A specific example of a group $Z^1$ is a divalent group of formula (6a)

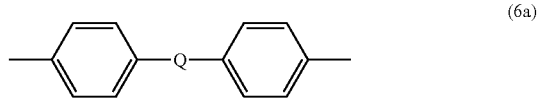

(6a)

wherein Q is —O—, —S—, —C(O)—, —SO$_2$—, —SO—, or —C$_y$H$_{2y}$— wherein y is an integer from 1 to 5 or a halogenated derivative thereof (including a perfluoroalkylene group). In a specific embodiment Q in formula (6) is 2,2-isopropylidene. The alkali metal salt (11) can be obtained by reaction of the metal hydroxide or carbonate with an aromatic dihydroxy compound of formula (12)

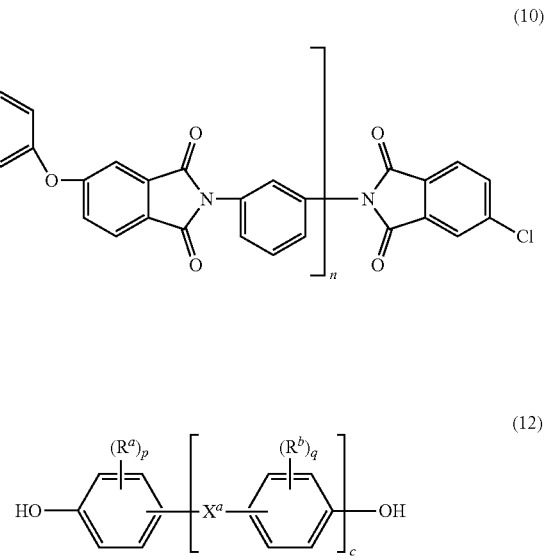

(12)

wherein $R^a$, $R^b$, $X^a$, and c are as described in formula (6). In an embodiment, the dihydroxy compound 2,2-bis(4-hydroxyphenyl) propane ("bisphenol A" or "BPA") can be used. A molar ratio of the reactive intermediates to the alkali metal salt (11) can be 0.9:1 to 1.1:1.

In an embodiment, the polymerization is conducted in the presence of a chain terminating agent. The chain terminating agent can be formed during imidization by the addition of a monofunctional compound as described above, or can be added after imidization. Such chain terminating agents include a monofunctional bisphthalimide, or an alkali metal salt of a monohydroxy aromatic compound of formula (13)

$$M^2O-Z^2 \tag{13}$$

wherein $M^2$ is for example lithium, sodium, potassium, or cesium. In an embodiment, $M^2$ is potassium or sodium, preferably sodium. $Z^2$ in formula (13) can be, for example, a group of formulas (14)

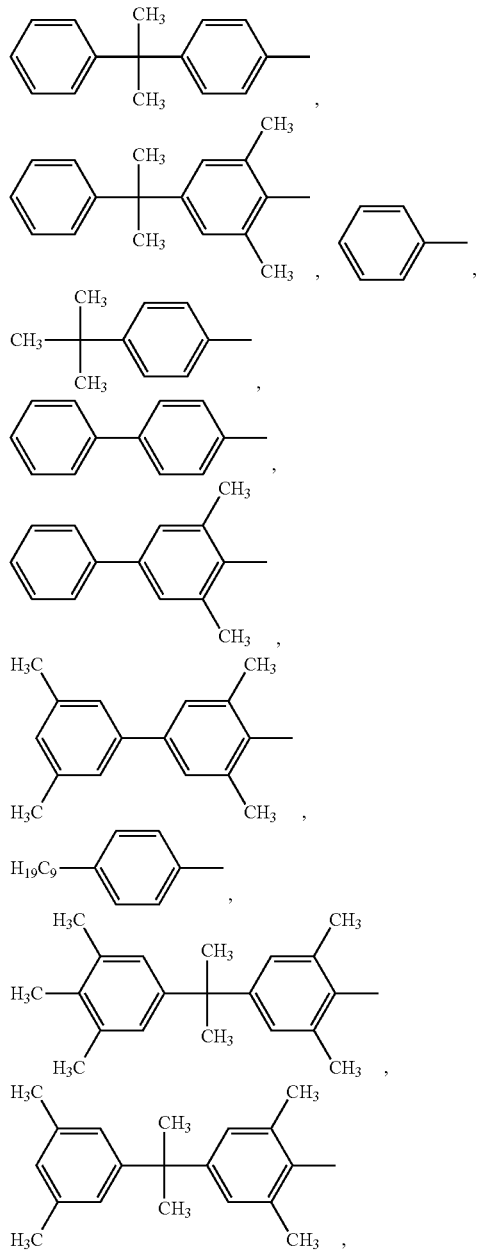

(14)

or a combination comprising at least one of the foregoing. The chain terminating agents are useful to control the type of end group in the polymer and to control the molecular weight of the polymer.

The polymerization can be conducted under conditions known to be effective to produce the polyetherimides. Such conditions are described, for example, in U.S. Pat. Nos. 6,235,866 and 6,265,521.

In general, the polymerization can be conducted in a relatively apolar, aprotic solvent with a boiling point above 100° C. or above 150° C. Suitable solvents include, but are not limited to, oDCB, dichlorotoluene, 1,2,4-trichlorobenzene, diphenyl sulfone, sulfolane, or a monoalkoxybenzene such as anisole, veratrole, diphenylether, or phenetole. In an embodiment, the solvent is oDCB. One or more of the other solvents can optionally be present with the oDCB, provided that the solvent(s) do not substantially adversely affect the desired solubilities.

The polymerization can be conducted in the presence of a phase transfer catalyst that is substantially stable under the reaction conditions used, in particular temperature. The phase transfer catalyst can be the same as the catalyst used in imidization, or different. Exemplary phase transfer catalysts for polymerization include guanidinium salts such as hexa($C_{1-8}$alkyl)guanidinium and α,ω-bis(penta($C_{1-8}$alkyl)guanidinium)alkane salts. The counterion can be nitrite, nitrate, mesylate, tosylate, or a halide, for example chloride. An exemplary catalyst is hexaethylguanidinium chloride (HEGCl).

Polymerization can be conducted at least 110° C., preferably 150° C. to 275° C., or 175° C. to 225° C. At temperatures below 110° C., reaction rates may be too slow for economical operation. Atmospheric or super-atmospheric pressures can be used, for example, up to 5 atmospheres, to facilitate the use of high temperatures without causing solvent to be lost by evaporation.

In an embodiment, the alkali metal salt (11), optionally a chain terminating agent, and the phase transfer catalyst are added directly to the reactive intermediate composition.

Polymerization produces a polyetherimide of formula (15)

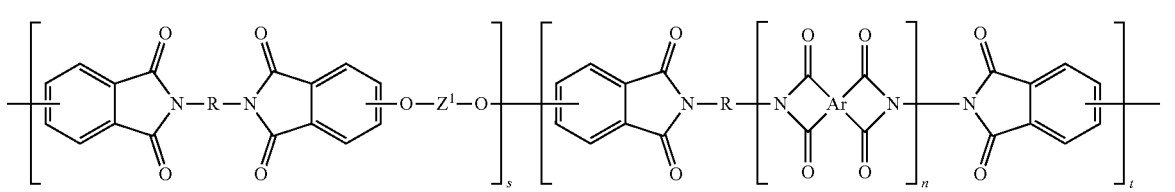

(15)

wherein s+t is 2 or more, or 5 or more, for example 2 to 1000, or 5 to 500, or 10 to 100, and R, Ar, and $Z^1$ are as defined above in Formulas (2), (4), and (6).

In an embodiment, the structure of the aromatic dianhydride (4) corresponds to the structure of the alkali metal salt of the dihydroxy aromatic compound (12). In these embodiments, the group Ar in the aromatic dianhydride (4) is of formula (16)

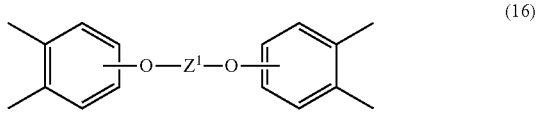
(16)

wherein $Z^1$ is the same as in the dialkali metal salt of the hydroxy aromatic compound (12). In this embodiment the polyetherimide is of formula (17)

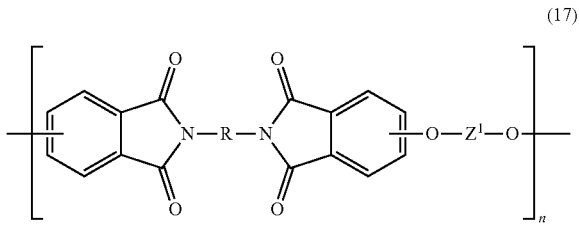
(17)

wherein n is 2 or more, or 5 or more, for example 2 to 1,000, or 5 to 500, or 10 to 100.

In an embodiment, the polymerization produces 15 to 40 wt % polyetherimide, or 17 to 35 wt % polyetherimide. In an embodiment, the polymerization produces 20 to 30 wt % polyetherimide on a solids basis with respect to the total weight of solvent and polymer produced.

In any of the foregoing embodiments, the polyetherimides can have a melt index of 0.1 to 10 grams per minute (g/min), as measured by American Society for Testing Materials (ASTM) D1238 at 340 to 370° C., using a 6.7 kilogram (kg) weight. In an embodiment, the polyetherimides have a weight average molecular weight (Mw) of 1,000 to 150,000 grams/mole (Dalton), as measured by gel permeation chromatography, using polystyrene standards. In an embodiment, the polyetherimide has an Mw of 10,000 to 80,000 Daltons. Such polyetherimides typically have an intrinsic viscosity greater than 0.2 deciliters per gram (dl/g), or, more specifically, 0.35 to 0.7 dl/g as measured in m-cresol at 25° C. The polyetherimides can have a polydispersity index (PDI) of 2.1 to 2.5, or 2.2 to 2.4, and a PDI* of 1.1 to 1.9, or 1.3 to 1.7.

The following non-limiting Examples further illustrate the methods and compositions disclosed herein.

EXAMPLES

Materials used in the Examples are listed in Table 1.

TABLE 1

| Designation | Chemical Description | Source |
| --- | --- | --- |
| DDS | 4,4-Diaminodiphenyl sulfone | Aldrich |
| mPD | meta-Phenylene diamine | Dupont |
| 4-ClPA | 4-Chlorophthalic anhydride | SABIC |

TABLE 1-continued

| Designation | Chemical Description | Source |
| --- | --- | --- |
| 3-ClPA | 3-Chlorophthalic anhydride | SABIC |
| PA | Phthalic anhydride | Aldrich |
| $H_3PO_4$ | Phosphoric Acid | Fischer |
| $Na_2BPA$ | Disodium Bisphenol A | SABIC |
| oDCB | o-Dichlorobenzene | Fischer |
| HEGCl | Hexaethylguanidinium chloride | SABIC |
| BPADA | Bisphenol A dianhydride | SABIC |

Amounts listed in the Examples are in weight percent (wt. %), based on the total weight of the identified composition.

Example 1

A one-liter, 3-necked, round-bottomed flask equipped with a mechanical stirrer, a Dean and Stark receiver topped with a reflux condenser, and means for maintaining a nitrogen sweep, was charged with oDCB (434 grams (g)), BPADA (7.8086 g, 0.015 mol), and 4-ClPA (48.7980 g, 0.267 mol); 10% of the anhydride functionality present in the flask was in the form of BPADA. Then, mPD (16.2211 g, 0.15 mol) and HEGCl (1.2955 mmol, 0.342 g) were added to the flask, and the flask was flushed with nitrogen for 10 minutes. The flask was heated to 185° C. with the use of an external oil bath. Water and oDCB were condensed overhead and removed from the collection arm of the receiver. The bulk of the water recovered from the reaction ceased after 1 hour at reflux. The moisture concentration in the condensed overheads after two hours was 15 ppm. A total of 65 g of oDCB was taken overhead during the reaction time. The mixture was refluxed for 3 hours to afford a nearly soluble mixture. No sticking of the bisphthalimide intermediates was observed inside the vessel. oDCB was removed by distillation until the % solids of the bisphthalimide intermediates in the vessel was 17 wt. %. The nitrogen sweep was adjusted to a minimum to avoid any further concentration of the bisphthalimide intermediates. The mixture was maintained at 180° C.

A separate vessel, configured as described above except that the mechanical stirrer was exchanged for a magnetic stir bar, was charged with 242.58 g of a 14.54 wt % slurry of bisphenol A disodium salt (35.27 grams, 0.1297 mol) in oDCB and an additional 28.82 g of oDCB under nitrogen. The vessel was heated to reflux with the use of an external oil bath and magnetically stirred. A total of 25 mL of oDCB was taken overhead. The moisture concentration in the condensed overheads after 25 mL had been taken overhead was 16 ppm. The oil bath was maintained at 180° C., and was then cannulated with the use of nitrogen pressure into the vessel containing the bischloro oligomeric polyimide over a 12 minute period. The flask was then rinsed with 30 mL of dry oDCB, and then this oDCB was cannulated into the polymerization vessel. Immediately after the oDCB rinse was added to the vessel, 1.10 g (1.25 wt % with respect to the amount of polymer produced) of dry potassium phosphate, wherein 90% of the particles of KP were <70 microns in diameter, was added to the reaction mixture. The oil bath on the polymerization vessel was held at 200° C. The reaction mixture was translucent within 20 minutes, indicating that all the BPA disodium salt had reacted.

The polymerization was allowed to proceed for 8 hours. The molecular build was followed over time by gel permeation chromatography (GPC), FIG. 1. The reaction reached an Mw plateau in roughly 3 hours. After 8 hours of reaction time, 120 mL of oDCB was added to the vessel. The polymerization was then quenched with $H_3PO_4$ (1.512 g of 85% $H_3PO_4$) at 160° C. for 1 hour. The final Mw of the polymer was 40318 with a PDI of 2.390 and a PDI* (Mz/Mw) of 1.514, as determined by GPC. The polymer contained 1.64 wt % of material below 2000 Daltons, and 3.60 wt % below 4000 Daltons.

Example 2

The imidization was repeated as described above for Example 1, except that 20% of the anhydride present was from BPADA. The resulting composition comprising the reactive intermediates was nearly soluble in oDCB at 180° C. at 17% solids.

Example 3

The imidization was repeated as describe herein above for Example 1, except that 50% of the anhydride present was from BPADA. The resulting composition comprising the reactive intermediates was completely soluble in oDCB at 180° C. at 17% solids.

Example 4

A one-liter, 4-necked jacketed reactor, equipped with a mechanical stirrer, a Dean Stark receiver topped with a reflux condenser, a solvent replenishment system and means for maintaining a nitrogen sweep, was charged with 4-ClPA (125.61 g); and oDCB (700 g). The agitator speed was set at 300 rpm, and the reactor was heated to 140° C. with the use of an oil bath that circulates hot oil through the reactor jacket, and 0.2 mol % of HEGCl was then added to the reactor, followed by slow addition of mPD (37 gr) over 1.5 hours. The initial % solids content in the reactor was 17.5%. After the mPD addition was completed, the oil bath was heated to 185° C. and a water/oDCB mixture was condensed overhead and removed from the collection arm of the receiver. The mixture was maintained at 180° C. and during that time, a mixture of reaction water and oDCB was continuously removed through the Dean Stark receiver. After 6 hours, the moisture concentration in the Dean Stark was <50 ppm. Next, 0.8 mol % of additional HEGCl was added to the reactor and the reaction continued for one extra hour. Total duration of the reaction was 7 hours and a final content of 19% solids was achieved.

Example 5

A one-liter, 4-necked jacketed reactor, equipped with a mechanical stirrer, a Dean Stark receiver topped with a reflux condenser, a solvent replenishment system, and means for maintaining a nitrogen sweep, was charged with 134.55 g of 4-ClPA; 11 g of bisphenol A diphthalic anhydride (BPADA) and 700 g of oDCB. The agitator speed was set at 300 rpm, and the oil bath was heated to 140° C. with the use of an oil bath that circulates hot oil through the reactor jacket, and 0.2 mol % of HEGCl was then added to the reactor, followed by slow addition of 42 g of mPD during 1.5 hours. The initial % solids content in the reactor was 20% and total of 5 mol % of the anhydride functionality present in the flask was in the form of BPADA. After the mPD addition was completed, the oil bath was heated to 185° C. and water/oDCB mixture was condensed overhead and removed from the collection arm of the receiver. The mixture was maintained at 180° C. and during that time, a mixture of reaction water and oDCB was continuously removed through the Dean Stark receiver. After 6 hours, the moisture concentration in the Dean Stark was <50 ppm. Next, 0.8 mol % additional HEGCl was added to the reactor and the reaction continued for one extra hour. Total duration of the reaction was 7 hours and a final content of 22% solids was achieved.

Example 6

The same imidization reaction procedure as described for Example 5 was followed, but increasing the batch size, using a charge 151.15 g of 4-ClPA, 25 g of BPADA, 700 g of oDCB and 50 g of mPD. The initial % solids content in the reactor was 22.5% and total of 10 mol % of the anhydride functionality present in the flask was in the form of BPADA. After 7 hours, the reaction was completed and a final content of 26% solids was achieved.

Batches prepared at 17.5% and 20% initial solids also yielded 26% final solids.

Example 7

The same imidization reaction procedure as described for Example 5 was followed, but increasing the batch size, using a charge 147.18 g of 4-ClPA, 55 g of BPADA, 700 g of oDCB and 55 g of mPD. The initial % solids content in the reactor was 25% and total of 20 mol % of the anhydride functionality present in the flask was in the form of BPADA. After 7 hours, reaction was completed and a final content of 31% solids was achieved.

Batches prepared at 17.5%, 20%, and 22.5% initial solids also yielded 31% final solids.

Example 8

The same imidization reaction procedure as described for Example 5 was followed, but increasing the batch size, using a charge 165.61 g of 4-ClPA, 78 g of BPADA, 700 g of oDCB and 65 g of mPD. The initial % solids content in the reactor was 27.5% and total of 25 mol % of the anhydride functionality present in the flask was in the form of BPADA. After 7 hours, the reaction was completed and a final content of 32% solids was achieved.

Batches prepared at 17.5%, 20%, 22.5%, and 25% initial solids also yielded 32% final solids.

Example 9

The same imidization reaction procedure as described for Example 5 was followed, but increasing the batch size, with a charge 173.42 g of 4-ClPA, 110 g of BPADA, 750 g of oDCB and 74 g of mPD. The initial % solids content in the reactor was 30% and total of 30 mol % of the anhydride functionality present in the flask was in the form of BPADA. After 7 hours, the reaction was completed and a final content of 34% solids was achieved.

Example 10

The same imidization reaction procedure as described for Example 5 was followed, but increasing the batch size, with a charge 155.36 g of 4-ClPA, 150 g of BPADA, 750 g of oDCB and 78 g of mPD. The initial % solids content in the reactor was 30% and total of 40 mol % of the anhydride functionality present in the flask was in the form of BPADA. After 7 hours, the reaction was completed and a final content of 37% solids was achieved.

Batches prepared at 17.5%, 20%, 22.5%, 25%, 27.5%, 30%, and 32.5% initial solids also yielded 37% final solids.

The bisphthalimide intermediates of Examples 4 to 10 were polymerized following the next general procedure: a compensated addition funnel was charged with the desired amount of BPA disodium salt/oDCB slurry at 24% solids, attached to one of the reactor necks and the contents of the addition funnel was discharged to the reactor under nitrogen. The discharge operation required about 30 minutes to complete. The reactor was kept at reflux and the polymerization was allowed to proceed until the reaction reached a Mw plateau in the 43,000-47,000 Da range. At that point, the polymerizations were quenched with $H_3PO_4$ (2.35 g of 85% $H_3PO_4$) at 160° C. for 1 hour.

The data obtained from Examples 4 to 10, respectively, is presented in Table 2.

TABLE 2

| Example No. | BPADA (mol %) | Initial solids (%) | Final solids (%) | mPD (g) | Polymer batch size (g) |
|---|---|---|---|---|---|
| 4 | 0 | 17.5 | 19 | 37 | 203 |
| 5 | 5 | 20 | 22 | 42 | 230 |
| 6 | 10 | 22.5 | 26 | 50 | 274 |
| 7 | 20 | 25 | 31 | 55 | 301 |
| 8 | 25 | 27.5 | 32 | 65 | 356 |
| 9 | 30 | 30 | 34 | 74 | 406 |
| 10 | 40 | 30 | 37 | 78 | 427 |

The data in Table 2 show that both the initial and final % solids in the imidization reactions could be increased by increasing the concentration of BPADA. In Examples 5 to 10, the initial solids were 20 to 30% and the final solids were 22 to 37%. Without BPADA (Example 4), the amount of initial solids was limited to 17.5% and final solids were limited to 19%, due to the high viscosity of the reaction mixtures.

The data show that an increase in the mol % of BPADA in the formulation allows an increase in the amount of mPD, allowing the reactions to proceed at higher % solids at the start (initial solids) leading to larger batch sizes (polymer batch size) while keeping the rest of the process conditions unchanged (e.g., agitation rpm, temperature).

Example 11

A one-liter, 4-necked jacketed reactor, equipped with a mechanical stirrer, a Dean Stark receiver topped with a reflux condenser, a solvent replenishment system and means for maintaining a nitrogen sweep, was charged with 96.71 g (0.53 mol) of of 4-ClPA; 30.18 g (0.279 mol) of mPD and oDCB as reaction solvent. The reactor was heated in an oil bath to 185° C. with the use of an oil bath that circulates hot oil through the reactor jacket. Water and oDCB were condensed overhead and removed from the collection arm of the receiver. Then, 6.16 g (0.0139 mol) of 4,4'-(hexafluoroisopropylidene) diphthalic anhydride (6-FDA) were added one hour after mPD was charged, being present at the end in the reactor, a total of 5 mol % of the anhydride functionality in the form of the 6-FDA, and 0.2 mol % of HEGCl was charged to the reactor as reaction catalyst. The oil bath was maintained at 180° C. for 6 hours, and during that time a mixture of reaction water and oDCB was continuously removed through the Dean Stark receiver. Then, an additional 0.8 mol % HEGCl was added to the reactor and the reaction continued for another hour. The total duration of the reaction was 7 hours, and fresh oDCB was added continuously to the reactor to keep the solids content at 11%.

A compensated addition funnel was charged with 306 g of a BPA disodium salt/oDCB slurry containing 67.32 g of pure BPA disodium salt on a dry basis, and then was attached to one of the reactor necks and the content discharged to the reactor under nitrogen. The discharge operation was completed in about 30 minutes. The reactor was maintained at reflux and the polymerization was allowed to proceed until the reaction reached a Mw plateau of 55,571 Da. The polymerization was then quenched with $H_3PO_4$ (2.35 g of 85% $H_3PO_4$) at 160° C. for 1 hour. The final Mw of the polymer was 54,477 Da with a Tg of 224.1° C.

Example 12

The same imidization protocol as described for Example 11 was used, with the charges: 96.2 g of 4-ClPA, 30 g of mPD, 4.47 g of benzophenone-3,3',4,4'-tetracarboxylic dianhydride (BTDA) and oDCB as reaction solvent. A total of 5 mol % of the anhydride functionality was in the form of the BTDA.

The product of the imidization reaction was then polymerized after charging 297.5 g of BPA salt slurry containing 67.09 g of BPA disodium salt on a dry basis following the described procedure in Example 11 and the reaction reached a Mw plateau of 54,893 Da. The polymerization was then quenched with $H_3PO_4$ (2.37 g of 85% $H_3PO_4$) at 160° C. for 1 hour. The final Mw of the polymer was 54,105 Da with a Tg of 222.47° C.

Example 13

The same imidization protocol described in Example 11 was used with the charges: 96.11 g of 4-ClPA, 30.1 g of mPD, 3.45 g of bicyclo[2.2.2]oct-7-ene-2,3,5,6-tetracarboxylic dianhydride (BOTDA) and oDCB as reaction solvent. A total of 5 mol % of the anhydride functionality was in the form of the BOTDA. The product of the imidization reaction was polymerized after charging 295 g of BPA salt slurry containing 67.13 g of pure BPA disodium salt on a dry basis following the described procedure in example 8 and the reaction reached reached a Mw plateau of 54,825 Da. The polymerization was then quenched with $H_3PO_4$ (2.33 g of 85% $H_3PO_4$) at 160° C. for 1 hour. The final Mw of the polymer was 54,223 Da with a Tg of 222.05° C.

The collective data for Examples 11 to 13 are presented in Table 3.

TABLE 3

| | Aromatic Dianhydride (DA) | 6-FDA | BTDA | BOTDA |
|---|---|---|---|---|
| Imidization | % Solids | 11% | 11% | 11% |
| | Mol % DA | 5% | 5% | 5% |
| Polymerization | Mw Quenched (Da) | 54,477 | 54,105 | 54,223 |
| | Solubility (oDCB) | Yes | Yes | Yes |
| | Tg (° C.) | 224.1 | 222.47 | 222.05 |

The results of Examples 11 to 13 show that the imidization reaction can be extended to a variety of aromatic dianhydrides in addition to BPADA. Additionally, an increase in Tg was observed.

Example 14

A one-liter, 4-necked jacketed reactor, equipped with a mechanical stirrer, a Dean Stark receiver topped with a reflux condenser, a solvent replenishment system and means for maintaining a nitrogen sweep, was charged with 120.4 g of 3-ClPA; 101.7 g of 4,4'-diaminodiphenylsulfone (DDS); 42.617 g of BPADA and 1340 g oDCB as reaction solvent. The reactor was heated to 185° C. with the use of an oil bath that circulates hot oil through the reactor jacket. Water and oDCB were condensed overhead and removed from the collection arm of the receiver for 2 hours and then 0.83 ml of HEGCl/oDCB solution at 20% solids were charged to catalyze the reaction. An additional 11.63 g of 3-ClPA was then added to the reactor. A total of 20 mol % of the anhydride functionality was in the form of BPADA. Then, an additional 3.32 ml HEGCl/oDCB solution at 20% solids was charged and the oil bath was maintained at 180° C. for 7 hours, and during that time a mixture of reaction water and oDCB were continuously removed through the Dean Stark receiver. The total duration of the reaction was 7 hours, and fresh oDCB was added continuously to the reactor to keep the solids content at 14% solids.

A compensated addition funnel was charged with 365.6 g of a BPA disodium salt/oDCB slurry containing 85.5 g of BPA disodium salt on a dry basis, and then was attached to one of the reactor necks and the contents discharged to the reactor under nitrogen. The discharge operation required about 30 minutes to complete. The reactor was kept at reflux and the polymerization was allowed to proceed until the reaction reached a Mw plateau at 50831 Da. The polymerization was then quenched with $H_3PO_4$ (2.2 ml of 85% $H_3PO_4$) at 160° C. for 1 hour. Then, 654 g of veratrole were charged to the reactor to keep the polymer in the solution, with a final solvent ratio of 40:60 (veratrole: oDCB) at 20% polymer solids content.

Example 15

The same imidization protocol as described for Example 14 was used, with the charges: 143 g of 3-ClPA; 101.3 g of 4,4'-diaminodiphenylsulfone (DDS); 10.5 g of BPADA and 1340 g oDCB as reaction solvent A total of 5 mol % of the anhydride functionality is in the form of the BPADA. The reactive composition was then polymerized after charging 363.1 g of a BPA salt slurry containing 84.9 g of BPA disodium salt on a dry basis following the described procedure in Example 14 and the reaction reached a Mw plateau of 52,290 Da. The polymerization was then quenched with $H_3PO_4$ (2.2 ml of 85% $H_3PO_4$) at 160° C. for 1 hour. Then, 650 g of veratrole were charged to the reactor to keep the polymer in the solution, with a final solvent ratio of 40:60 (veratrole:oDCB) at 20% polymer solids content. The final Mw of the polymer was 50,920 Da with a Tg of 263.05° C.

Example 16

The same imidization protocol as described for Example 14 was followed, with the charges: 84.15 g of 3-ClPA; 60 g of 4,4'-diaminodiphenylsulfone (DDS); 3.55 g of biphenol diphtalic anhydride (BPDA) and 790 g oDCB as reaction solvent. A total of 5 mol % of the anhydride functionality was in the form of the BPDA. The reactive composition was then polymerized after charging 250.45 g of a BPA salt slurry containing 58.78 g of BPA disodium salt on a dry basis following the described procedure in Example 14 and the reaction reached a Mw plateau of 55,706 Da. The polymerization was then quenched with $H_3PO_4$ (1.3 ml of 85% $H_3PO_4$) at 160° C. for 1 hour. Then, 380 g of veratrole was charged to the reactor to keep the polymer in the solution, with a final solvent ratio of 40:60 (veratrole: oDCB) at 20% polymer solids content. The final Mw of the polymer was 51,225 Da with a Tg of 271.6° C.

Example 17

The same imidization protocol as described for Example 14 was followed, with the charges: 83.58 g of 3-ClPA; 60.1 g of 4,4'-diaminodiphenylsulfone (DDS); 5.35 g of 6-FDA and 790 g oDCB as reaction solvent A total of 5 mol % of the anhydride functionality was in the form of the 6-FDA. The reactive composition was then polymerized after charging 248.3 g of a BPA salt slurry containing 58.27 g of BPA disodium salt on a dry basis following the described procedure in Example 14 and the reaction reached a Mw plateau of 51,181 Da. The polymerization was then quenched with $H_3PO_4$ (1.3 ml of 85% $H_3PO_4$) at 160° C. for 1 hour. Then, 380 g of veratrole was charged to the reactor to keep the polymer in the solution, with a final solvent ratio of 40:60 (veratrole: oDCB) at 20% polymer solids content. The final Mw of the polymer was 48,651 Da with a Tg of 270.69° C.

Example 18 and 19

The same imidization protocol as described for Example 14 was used, with the charges: 83.6 g of 3-ClPA; 60 g of 4,4'-diaminodiphenylsulfone (DDS); 3.89 g of BTDA and 790 g oDCB as reaction solvent A total of 5 mol % of the anhydride functionality was in the form of the BTDA. The reactive composition was then polymerized after charging 258.1 g of a BPA salt slurry containing 58.89 g of BPA disodium salt on a dry basis following the described procedure in Example 14 and the reaction reached a Mw plateau of 55,101 Da. The polymerization was then quenched with $H_3PO_4$ (1.3 ml of 85% $H_3PO_4$) at 160° C. for 1 hour. Then, 380 g of veratrole was charged to the reactor to keep the polymer in the solution, with a final solvent ratio of 40:60 (veratrole: oDCB) at 20% polymer solids content. The final Mw of the polymer was 55,474 Da with a Tg of 269.35° C.

A similar imidization protocol as described above was used to provide a second data point for BTDA.

Data from Examples 16 to 19 are presented in Table 4.

TABLE 4

| Imidization | Aromatic Dianhydride (DA) | BPDA | 6FDA | BTDA | BTDA |
|---|---|---|---|---|---|
| | % Solids | 14% | 14% | 14% | 14% |
| | Mol % DA | 5% | 5% | 5% | 10% |
| Polymerization | Mw Quenched (Da) | 51,225 | 48,651 | 55,474 | 54,058 |
| | Solubility (veratrole) | Yes | Yes | Yes | Yes |
| | Tg (° C.) | 271.65 | 270.69 | 269.35 | 271.74 |

The results of Examples 16 to 18 indicate that the imidization reaction can be extended to a variety of diamines and aromatic dianhydrides. Additionally, an increase in Tg was observed.

The claims are further illustrated by the following aspects.

Aspect 1. A method for producing a reactive intermediate composition, including: reacting a substituted phthalic anhydride of the formula

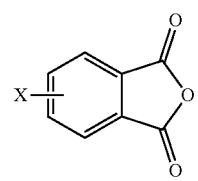

with a diamine of the formula $H_2N-R-NH_2$ in the presence of an aromatic dianhydride in an amount of 10 to 50 mole percent based on the total moles of anhydride functionality in the reaction; wherein the reacting is conducted in an aprotic solvent in a reactor, under conditions effective to produce the reactive intermediate composition; and wherein X comprises a halogen or a nitro group, and R comprises a $C_{6-20}$ aromatic hydrocarbon group or a halogenated derivative thereof, a straight or branched chain $C_{2-20}$ alkylene or a halogenated derivative thereof, or a $C_{3-8}$ cycloalkylene or a halogenated derivative thereof.

Aspect 2. The method of Aspect 1, wherein the aprotic solvent comprises o-dichlorobenzene, dichlorotoluene, 1,2,4-trichlorobenzene, diphenyl sulfone, sulfolane, anisole, veratrole, diphenylether, phenetole, or a combination comprising at least one of the foregoing aprotic solvents, or preferably wherein the aprotic solvent comprises o-dichlorobenzene.

Aspect 3. The method of Aspect 1 or Aspect 2, wherein a molar ratio of total anhydride groups to diamine is 1.98:1 to 2.2:1, preferably 2:1 to 2.1:1.

Aspect 4. The method of any one or more of Aspects 1 to 3, wherein the reacting is in the presence of a phase-transfer catalyst; in the presence of an monoanhydride, monoamine, or monopthalimide chain terminating agent; at a temperature of at least 110° C., or 150° C. to 275° C., preferably 175° C. to 225° C.; and under a pressure of up to 45 pounds per square inch (gauge) (up to 310 kilopascal), or 1 to 10 psig (6.89 to 68.9 kilopascal), preferably 3 to 7 psig (20.7 to 48.3 kilopascal).

Aspect 5. The method of any one or more of Aspects 1 to 4, wherein the components of the intermediate composition adhere to a wall of the reactor less than in the components of an intermediate composition obtained by the same reaction conducted under the same conditions except in the absence the aromatic dianhydrides resulting in less residual monomers in the final polymer and a faster polymerization reaction time, and at a higher wt. % solids content allowing for more throughput in a manufacturing facility.

Aspect 6. The method of any one or more of Aspects 1 to 5, wherein a solubility of the components of the intermediate reaction composition at 180° C. is greater than a solubility of the components of an intermediate composition at 180° C. that is obtained by the same reaction conducted under the same conditions except without the aromatic dianhydride.

Aspect 7. The method of any one or more of Aspects 1 to 6, wherein a weight percent of solids for the intermediate reaction composition at 180° C. is greater than a weight percent of solids for an intermediate composition at 180° C. that is obtained by the same reaction conducted under the same conditions except without the aromatic dianhydride.

Aspect 8. The method of any one or more of Aspects 1 to 7, wherein the amount of the aromatic dianhydride is from 10 to 35 mole percent, based on the total moles of anhydride functionality, preferably wherein the amount of the aromatic dianhydride is from 20 to 30 mole percent, based on of the total moles of the anhydride functionality.

Aspect 9. The method of any one or more of Aspects 1 to 8, wherein the aromatic dianhydride is of the formula

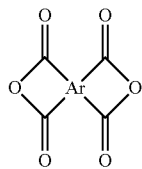

wherein Ar is a tetravalent $C_{6-36}$ hydrocarbon comprising at least one aromatic group, preferably wherein Ar is a group of the formula

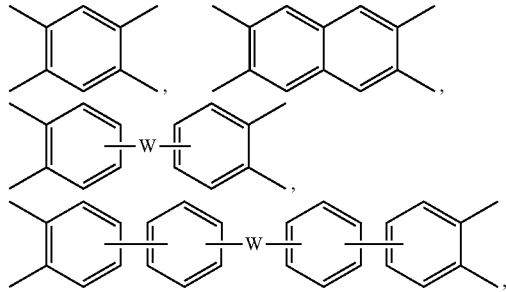

wherein W is a single bond, $-O-$, $-S-$, $-C(O)-$, $-SO_2-$, $-SO-$, a $C_{1-18}$ hydrocarbon, or $-O-Z-O-$ wherein Z is a $C_{1-12}$ hydrocarbon, preferably wherein W is a single bond, $-O-$, $-S(O)-$, $-S(O)_2-$, $-C(O)-$, phenylene, $-OC_6H_4O-$, or $-O-Z-O-$ wherein Z is a $C_{3-12}$ alkylidene or $C_{4-12}$ cycloalkylidene having a ring size of 4 to 6 carbon atoms.

Aspect 10. The method of Aspect 9, wherein the aromatic dianhydride is 4,4'-bisphenol A dianhydride, 3,4'-bisphenol A dianhydride, 3,3'-bisphenol A dianhydride, bis[4-(2,3-dicarboxyphenoxy)phenyl]propane dianhydride, 2,2-bis[4-(3,4-dicarboxyphenoxy)phenyl]butane dianhydride, 4,4'-oxydiphthalic anhydride, 1,1,1,3,3,3-hexafluoro-2,2-bis[4-(3,4-dicarboxyphenoxy)phenyl]propane dianhydride, 4,4'-(hexafluoroisopropylidene)diphthalic anhydride, pyromellitic dianhydride, hydroquinone diphthalic anhydride, 3,3',4,4'-diphenylsulfone tetracarboxylic dianhydride, 3,3',4,4'-benzophenone tetracarboxylic dianhydride, 3,3',4,4'-biphenyltetracarboxylic dianhydride, 5,5'-[[1,1'-biphenyl]-4,4'-diylbis(oxy)]bis-1,3-isobenzofurandione, 3,4,9,10-perylene-tetracarboxylic dianhydride, 1,4,5,8-naphthalenetetracarboxylic dianhydride, or a combination comprising at least one of the foregoing anhydrides; preferably wherein the aromatic dianhydride is 4,4'-bisphenol A dianhydride, 4,4'-oxydiphthalic anhydride, pyromellitic dianhydride, hydroquinone diphthalic anhydride, 3,3',4,4'-diphenylsulfone tetracarboxylic dianhydride, diphenylsulfone tetracarboxylic dianhydride, benzophenonetetracarboxylic dianhydride, biphenyltetracarboxylic dianhydride, or a combination comprising at least one of the foregoing anhydrides; more preferably wherein the aromatic dianhydride is bisphenol A dianhydride, oxydiphthalic dianhydride, pyromelletic dianhydride, biphenyltetracarboxylic dianhydride, or a combination comprising at least one of the foregoing anhydrides.

Aspect 11. The method of any one or more of Aspects 1 to 10, wherein the reactive polyetherimide intermediate is present in an amount of 15 to 35 weight percent solids based on a total weight of the reaction mass; preferably wherein the reactive polyetherimide intermediate is present in an amount of 20 to 30 weight percent solids, based on a total weight of the reaction components.

Aspect 12. The method of any one or more of Aspects 1 to 11, wherein X comprises a halogen; and R is a divalent group of formulas (3) wherein $Q^1$ is $-O-$, $-S-$, $-C(O)-$, $-SO_2-$, $-SO-$, $-P(R^a)(=O)-$ wherein $R^a$ is a $C_{1-8}$ alkyl or $C_{6-12}$ aryl, $-C_yH_{2y}-$ wherein y is an integer from 1 to 5 or a halogenated derivative thereof, or $-(C_6H_{10})_z-$ wherein z is 1 to 4.

Aspect 13. The method of any one or more of Aspects 1 to 12, wherein R is m-phenylene, p-phenylene, bis(4,4'-phenylene)sulfone, bis(3,4'-phenylene)sulfone, bis(3,3'-phenylene)sulfone, or a combination comprising at least one of the foregoing.

Aspect 14. The method of any one or more of Aspects 1 to 13, wherein the substituted phthalic anhydride comprises 4-chlorophthalic anhydride; the diamine is m-phenylene diamine, p-phenylene diamine, 4,4'-diaminodiphenyl sulfone, 3,4'-diaminodiphenyl sulfone, 3,3'-diaminodiphenyl sulfone, or a combination comprising at least one of the foregoing; and the aromatic dianhydride is bisphenol A dianhydride.

Aspect 15. The method of any one or more of Aspects 1 to 13, wherein the substituted phthalic anhydride comprises 3-chlorophthalic anhydride; the diamine is m-phenylene diamine, 4,4'-diaminodiphenyl sulfone, or a combination comprising at least one of the foregoing; and the aromatic dianhydride is bisphenol A dianhydride.

Aspect 16. A method for manufacturing a polyetherimide, comprising reacting the reactive intermediate composition obtained by the method of any one or more of Aspects 1 to 15 with an alkali metal salt of a dihydroxy aromatic compound in a polymerization mixture comprising an aprotic solvent and a phase transfer catalyst, under conditions effective to produce the polyetherimide.

Aspect 17. The method of Aspect 16, wherein the polymerization mixture further comprises an alkali metal salt of a monohydroxy aromatic compound.

Aspect 17. The method of Aspect 16 or 17, wherein the polyetherimide is present in an amount of 15 to 40 weight percent solids, based on a total weight of the polymerization mixture, preferably wherein the polyetherimide is present in an amount of 17 to 35 weight percent solids based on the total weight of the polymerization mixture.

The compositions, methods, and articles can alternatively comprise, consist of, or consist essentially of, any appropriate components or steps herein disclosed. The compositions, methods, and articles can additionally, or alternatively, be formulated so as to be devoid, or substantially free, of any components, materials, ingredients, adjuvants or species used in the prior art compositions or that are otherwise not necessary to the achievement of the function and/or objectives of the present claims.

All ranges disclosed herein are inclusive of the endpoints, and the endpoints are independently combinable with each other. "Combination" is inclusive of blends, mixtures, alloys, reaction products, and the like. The terms "a" and "an" and "the" do not denote a limitation of quantity, and are to be construed to cover both the singular and the plural, unless otherwise indicated herein or clearly contradicted by context. "Or" means "and/or" unless clearly stated otherwise. Reference throughout the specification to "an embodiment," and so forth, means that a particular element described in connection with the embodiment is included in at least one embodiment described herein, and may or may not be present in other embodiments. In addition, the described elements may be combined in any suitable manner in the various embodiments.

The term "alkyl" includes branched or straight chain, unsaturated aliphatic $C_{1-30}$ hydrocarbon groups e.g., methyl, ethyl, n-propyl, i-propyl, n-butyl, s-butyl, t-butyl, n-pentyl, s-pentyl, n- and s-hexyl, n- and s-heptyl, and, n- and s-octyl. "Alkenyl" means a straight or branched chain, monovalent hydrocarbon group having at least one carbon-carbon double bond (e.g., ethenyl (—HC=CH$_2$)). "Alkoxy" means an alkyl group that is linked via an oxygen (i.e., alkyl-O—), for example methoxy, ethoxy, and sec-butyloxy groups. "Alkylene" means a straight or branched chain, saturated, divalent aliphatic hydrocarbon group (e.g., methylene (—CH$_2$—) or, propylene (—(CH$_2$)$_3$—)). "Cycloalkylene" means a divalent cyclic alkylene group, —C$_n$H$_{2n-x}$, wherein x is the number of hydrogens replaced by cyclization(s). "Cycloalkenyl" means a monovalent group having one or more rings and one or more carbon-carbon double bonds in the ring, wherein all ring members are carbon (e.g., cyclopentyl and cyclohexyl). "Aryl" means an aromatic hydrocarbon group containing the specified number of carbon atoms, such as phenyl, tropone, indanyl, or naphthyl. The prefix "halo" means a group or compound including one more of a fluoro, chloro, bromo, or iodo substituent. A combination of different halo groups (e.g., bromo and fluoro), or only chloro groups can be present. The prefix "hetero" means that the compound or group includes at least one ring member that is a heteroatom (e.g., 1, 2, or 3 heteroatom(s)), wherein the heteroatom(s) is each independently N, O, S, or P. "Substituted" means that the compound or group is substituted with at least one (e.g., 1, 2, 3, or 4) substituents independently selected from a $C_{1-9}$ alkoxy, a $C_{1-9}$ haloalkoxy, a nitro (—NO$_2$), a cyano (—CN), a $C_{1-6}$ alkyl sulfonyl (—S(=O)$_2$-alkyl), a $C_{6-12}$ aryl sulfonyl (—S(=O)$_2$-aryl) a thiol (—SH), a thiocyano (—SCN), a tosyl (CH$_3$C$_6$H$_4$SO$_2$—), a $C_{3-12}$ cycloalkyl, a $C_{2-12}$ alkenyl, a $C_{5-12}$ cycloalkenyl, a $C_{6-12}$ aryl, a $C_{7-13}$ arylalkylene, a $C_{4-12}$ heterocycloalkyl, and a $C_{3-12}$ heteroaryl instead of hydrogen, provided that the substituted atom's normal valence is not exceeded.

All references are incorporated herein by reference.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications, variations, improvements, and substantial equivalents.

What is claimed is:

1. A method for producing a reactive intermediate composition, the method comprising
reacting a substituted phthalic anhydride of the formula

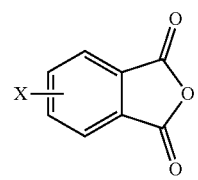

with a diamine of the formula

in the presence of an aromatic dianhydride in an amount of 10 to 50 mole percent based on the total moles of anhydride functionality in the reaction, and optionally a chain terminating agent;
wherein the reacting is conducted in an aprotic solvent in a reactor, under conditions effective to produce the reactive intermediate composition; and
wherein
X comprises a halogen or a nitro group, and
R comprises a $C_{6-20}$ aromatic hydrocarbon group or a halogenated derivative thereof, a straight or branched chain $C_{2-20}$ alkylene or a halogenated derivative thereof, or a $C_{3-8}$ cycloalkylene or a halogenated derivative thereof.

2. The method of claim 1, wherein the aprotic solvent comprises o-dichlorobenzene, dichlorotoluene, 1,2,4-trichlorobenzene, diphenyl sulfone, sulfolane, anisole, veratrole, diphenylether, phenetole, or a combination comprising at least one of the foregoing aprotic solvents.

3. The method of claim 1, wherein a molar ratio of total anhydride groups to diamine is 1.98:1 to 2.2:1.

4. The method of claim 1, wherein the reacting is
in the presence of a phase-transfer catalyst;
in the presence of an monoanhydride, monoamine, or mono-functionalized phthalimide chain terminating agent;
at a temperature of at least 110° C.; and
under a pressure of up to 310 kilopascal.

5. The method of claim 1, wherein the components of the intermediate composition adhere to a wall of the reactor less than in the components of an intermediate composition obtained by the same reaction conducted under the same conditions except in the absence the aromatic dianhydride.

6. The method of claim 1, wherein a solubility of the components of the intermediate reaction composition at 180° C. is greater than a solubility of the components of an intermediate composition at 180° C. that is obtained by the same reaction conducted under the same conditions except without the aromatic dianhydride.

7. The method of claim 1, wherein a weight percent of solids for the intermediate reaction composition at 180° C. is greater than a weight percent of solids for an intermediate composition at 180° C. that is obtained by the same reaction conducted under the same conditions except without the aromatic dianhydride.

8. The method of claim 1, wherein the amount of the aromatic dianhydride is from 10 to 35 mole percent, based on the total moles of anhydride functionality.

9. The method of claim 1, wherein the aromatic dianhydride is of the formula

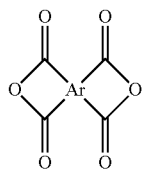

wherein Ar is a group of the formula

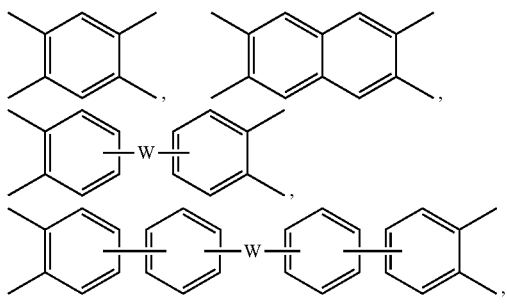

wherein W is a single bond, —O—, —S—, —C(O)—, —SO$_2$—, —SO—, a C1-12 hydrocarbon or —O—Z—O— wherein Z is a C1-12 hydrocarbon.

10. The method of claim 9, wherein the aromatic dianhydride is 4,4'-bisphenol A dianhydride, 3,4'-bisphenol A dianhydride, 3,3'-bisphenol A dianhydride, 2,2-bis[4-(2,3-dicarboxyphenoxy)phenyl]propane dianhydride, 2,2-bis[4-(3,4-dicarboxyphenoxy)phenyl]butane dianhydride, 4,4'-oxydiphthalic anhydride, 1,1,1,3,3,3-hexafluoro-2,2-bis[4-(3,4-dicarboxyphenoxy)phenyl[propane dianhydride, 4,4'-(hexafluoroisopropylidene)diphthalic anhydride, pyromellitic dianhydride, hydroquinone diphthalic anhydride, 3,3',4,4'-diphenylsulfone tetracarboxylic dianhydride, 3,3',4,4'-benzophenone tetracarboxylic dianhydride, 3,3',4,4'-biphenyltetracarboxylic dianhydride, 5,5'-[[1,1'-biphenyl]-4,4'-diylbis(oxy)]bis-1,3-isobenzofurandione, 3,4,9,10-perylene-tetracarboxylic dianhydride, 1,4,5,8-naphthalenetetracarboxylic dianhydride, or a combination comprising at least one of the foregoing anhydrides.

11. The method of claim 1, wherein the reactive intermediate is present in an amount of 15 to 40 weight percent solids based on a total weight of the reaction mass.

12. The method of claim 1, wherein
X comprises a halogen; and
R is a divalent group of the formulas

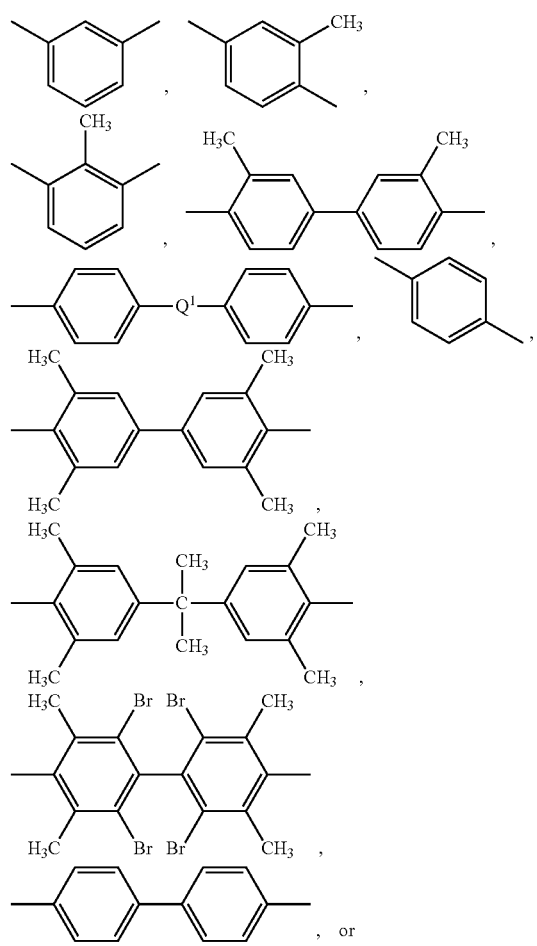

-continued

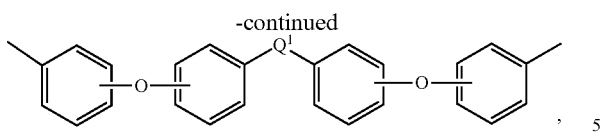, wherein $Q^1$ is —O—, —S—, —C(O)—, —SO$_2$—, —SO—, —P(R$^a$)(=O)— wherein R$^a$ is a C$_{1-8}$ alkyl or C$_{6-12}$ aryl, —C$_y$H$_{2y}$— wherein y is an integer from 1 to 5 or a halogenated derivative thereof, or —(C$_6$H$_{10}$)$_z$— wherein z is an integer from 1 to 4.

13. The method of claim 1, wherein R is m-phenylene, p-phenylene, bis(4,4'-phenylene)sulfone, bis(3,4'-phenylene)sulfone, bis(3,3'-phenylene)sulfone, or a combination comprising at least one of the foregoing.

14. The method of claim 1, wherein
the substituted phthalic anhydride comprises 4-chlorophthalic anhydride;
the diamine is m-phenylene diamine, p-phenylene diamine, 4,4'-diaminodiphenyl sulfone, 3,4'-diaminodiphenyl sulfone, 3,3'-diaminodiphenyl sulfone, or a combination comprising at least one of the foregoing; and
the aromatic dianhydride is bisphenol A dianhydride.

15. The method of claim 1, wherein
the substituted phthalic anhydride comprises 3-chlorophthalic anhydride;
the diamine is m-phenylene diamine, 4,4'-diaminodiphenyl sulfone, or a combination comprising at least one of the foregoing; and
the aromatic dianhydride is bisphenol A dianhydride.

* * * * *